US009784811B2

(12) United States Patent
Chen et al.

(10) Patent No.: US 9,784,811 B2
(45) Date of Patent: Oct. 10, 2017

(54) TWO-CHANNEL MAGNETIC RESONANCE IMAGING

(75) Inventors: Chih-Chung Chen, Zhunan Township, Miaoli County (TW); Klaus Huber, Effeltrich (DE); Johannes Reinschke, Nürnberg (DE); Claus Seisenberger, Neufrannhofen (DE); Markus Vester, Nürnberg (DE); Christian Wünsch, Röthenbach a.d.Pegnitz (DE)

(73) Assignee: Siemens Aktiengesellschaft, München (DE)

( * ) Notice: Subject to any disclaimer, the term of this patent is extended or adjusted under 35 U.S.C. 154(b) by 771 days.

(21) Appl. No.: 14/349,419

(22) PCT Filed: Sep. 12, 2012

(86) PCT No.: PCT/EP2012/067840
§ 371 (c)(1),
(2), (4) Date: Sep. 15, 2014

(87) PCT Pub. No.: WO2013/050223
PCT Pub. Date: Apr. 11, 2013

(65) Prior Publication Data
US 2015/0028870 A1    Jan. 29, 2015

(30) Foreign Application Priority Data
Oct. 6, 2011   (DE) .................. 10 2011 084 072

(51) Int. Cl.
*G01R 33/54* (2006.01)
*G01R 33/36* (2006.01)
(Continued)

(52) U.S. Cl.
CPC ............ *G01R 33/543* (2013.01); *A61B 5/055* (2013.01); *A61B 5/7225* (2013.01);
(Continued)

(58) Field of Classification Search
CPC .............. G01R 33/543; G01R 33/3614; G01R 33/365; A61B 5/055; A61B 5/7225; A61B 5/7271
See application file for complete search history.

(56) References Cited

U.S. PATENT DOCUMENTS

| 4,739,268 A | 4/1988 | Fox |
| 5,424,646 A | 6/1995 | Hoshino |

(Continued)

FOREIGN PATENT DOCUMENTS

| CN | 1864080 A | 11/2006 |
| CN | 101023368 A | 8/2007 |

(Continued)

OTHER PUBLICATIONS

Chinese Office Action for related Chinese Application No. 2012800596413, dated Jun. 30, 2015, with English Translation.
(Continued)

*Primary Examiner* — Rodney Bonnette
(74) *Attorney, Agent, or Firm* — Lempia Summerfield Katz LLC

(57) ABSTRACT

A two-channel magnetic resonance tomography system is provided with a regulation circuit for an amplification system in order to be able to take into account different load situations of the MRI system in a flexible and efficient manner. It is thus possible to improve the MRI measurements greatly if the MRI system is set to the respective load situation beforehand by an idle state measurement. The adaptation may optionally also be carried out during the MRI measurement. Therefore, a multiplicity of completely different load situations may be taken into account in an optimized manner by the regulation circuit.

18 Claims, 2 Drawing Sheets

(51) Int. Cl.
*A61B 5/055* (2006.01)
*A61B 5/00* (2006.01)
(52) U.S. Cl.
CPC .......... *A61B 5/7271* (2013.01); *G01R 33/365* (2013.01); *G01R 33/3614* (2013.01)

(56) References Cited

U.S. PATENT DOCUMENTS

| | | |
|---|---|---|
| 6,411,090 B1 | 6/2002 | Boskamp |
| 6,927,573 B2 | 8/2005 | Eberler et al. |
| 6,969,992 B2 | 11/2005 | Vaughan et al. |
| 7,397,243 B1 | 7/2008 | Bulkes et al. |
| 7,639,015 B2 | 12/2009 | Thuringer et al. |
| 2004/0150401 A1 | 8/2004 | Eberler et al. |
| 2007/0222449 A1 | 9/2007 | Hoult |
| 2007/0279058 A1 | 12/2007 | Bulkes et al. |
| 2008/0204027 A1 | 8/2008 | Luedeke et al. |
| 2008/0258728 A1 | 10/2008 | Vernickel et al. |
| 2008/0284436 A1 | 11/2008 | Weizenecker et al. |
| 2009/0128150 A1 | 5/2009 | Ham et al. |
| 2010/0106008 A1 | 4/2010 | Harvey |
| 2010/0141257 A1 | 6/2010 | Graesslin et al. |
| 2010/0148874 A1 | 6/2010 | Thuringer et al. |
| 2010/0244840 A1 | 9/2010 | McKinnon |

FOREIGN PATENT DOCUMENTS

| | | |
|---|---|---|
| CN | 101297211 A | 10/2008 |
| CN | 101467060 A | 6/2009 |
| CN | 101636664 A | 1/2010 |
| DE | 69223981 T2 | 6/1998 |
| DE | 10254660 A1 | 6/2004 |
| EP | 1852710 A2 | 11/2007 |
| JP | 61095237 A | 5/1986 |
| JP | 63192428 A | 8/1988 |
| JP | H0595929 A | 4/1993 |
| JP | 2003033332 A | 2/2003 |
| JP | 2007507719 A | 3/2007 |
| JP | 2010525855 A | 7/2010 |
| JP | 2010532136 A | 9/2010 |
| WO | WO2008114178 A1 | 9/2008 |
| WO | WO2008135872 A1 | 11/2008 |

OTHER PUBLICATIONS

Japanese Office Action for related Japanese Application No. 2014-533818, dated Apr. 3, 2015, with English Translation.
German Office Action cited in DE102011084072.9, dated Jul. 6, 2012.
International Search Report and Written Opinion cited in PCT/EP2012/067840, dated Dec. 12, 2012.
Magnetic Resonance Imaging, modified Mar. 14, 2014, Wikipedia.com.
Stang et al., RF Sensor Considerations for Input Predistortion Correction of Transmit Arrays, Jan. 1, 2010 p. 44, Proc. Intl Soc Mag Reson Med.
Stang et al., Vector Iterative Pre-Distortion: An Auto-Calibration Method for Transmit Arrays, Jan. 1, 2009, p. 396, Proc. Intl Soc Mag Reson Med 17.
Yan et al., Fast-Settling Amplifier Design Using Feedforward Compensation Technique, Aug. 8, 2008, pp. 494-497, vol. 1, Proc. 43rd IEEE Midwest Stmp. on Circuits and Systems.

TWO-CHANNEL MAGNETIC RESONANCE IMAGING

CROSS-REFERENCE TO RELATED APPLICATIONS

The present patent document is a §371 nationalization of PCT Application Serial Number PCT/EP2012/067840, filed Sep. 12, 2012, designating the United States, which is hereby incorporated by reference, and this patent document also claims the benefit of DE 10 2011 084 072.9, filed on Oct. 6, 2011, which is also hereby incorporated by reference.

TECHNICAL FIELD

The embodiments relate to methods for setting an amplification system for a two-channel magnetic resonance imaging system, and to an apparatus for driving a two-channel magnetic resonance imaging system.

BACKGROUND

Magnetic resonance imaging (MRI) is an imaging method that is used primarily in medical diagnostics for representing the structure and function of the tissues and organs in the body. MRI is based physically on the principles of the nuclear spin resonance and is therefore also designated as nuclear spin tomography.

MRI may be used to generate slice images of the human (or animal) body that allow an assessment of the organs and of many pathological organ changes. Magnetic resonance imaging is based on strong magnetic fields and alternating electromagnetic fields in the radio-frequency range that resonantly excite specific atomic nuclei (e.g., the hydrogen nuclei/protons) in the body, which then induce electrical signals in the receiver circuit. No burdensome X-ray radiation or other ionizing radiation is generated or used in the device. Different relaxation times of different types of tissue are an essential basis for the image contrast. In addition, the different content of hydrogen atoms in different tissues (e.g., muscle, bone) also contributes to the image contrast.

SUMMARY AND DESCRIPTION

The scope of the present invention is defined solely by the appended claims and is not affected to any degree by the statements within this summary. The present embodiments may obviate one or more of the drawbacks or limitations in the related art.

The approach proposed here relates, in particular, to voltage control or a device for voltage control for a radio-frequency power amplifier (RFPA) system such as is used in MRI.

The object of an embodiment is to improve MRI technology and to be able to optimize the MRI technology flexibly, in particular, toward different load situations (e.g., patients, organs, positions).

In order to achieve the object, a method for setting an amplification system for a two-channel magnetic resonance imaging system is specified, wherein the amplification system is adapted by a control circuit depending on a load situation.

Consequently, an RF excitation signal may be stabilized and a flexible optimization to different load situations may be achieved.

In certain embodiments, the amplification system includes a dedicated amplifier for each channel of the magnetic resonance imaging system.

The approach proposed here makes it possible to calibrate the two-channel magnetic resonance imaging system specifically to the respective load situation and thus to use a setting that is expedient for the load situation. This approach leads to a significant improvement in the measurement results and increases the flexibility of the two-channel magnetic resonance imaging system also with regard to body coils that may be used.

It is thus also possible to fulfill specific predefined stipulations (fast settling time while complying with a predefined maximum, exact or suitable amplification) even with regard to totally different load situations.

In one development, the control circuit has a feedback of the output signal of the amplification system, in particular, to the input of the amplification system.

The feedback may be used for setting controllers (control elements) in a feedforward branch of the control circuit.

In another development, a delay of the output signal is carried out during the feedback.

In particular, a delay element may be provided for this purpose.

In particular, in one development, with the aid of the amplification system, the load situation is determined and at least one controller of the two-channel magnetic resonance imaging system is set depending on the load situation.

In particular, the type of load situation or at least one parameter of the load situation may be determined (e.g. estimated) with the aid of a measurement, e.g. an open-loop measurement (measurement without closed-loop control).

In one development, moreover, the at least one controller includes a load-dependent feedforward controller for setting a suitable (in particular, maximum or exact) amplification of the amplification system.

The amplification of the amplification system may be set or controlled by the load-dependent feedforward controller. This makes it possible to provide, in particular, that a predefined maximum amplification is not exceeded.

Furthermore, in one development, the at least one controller includes a further load-dependent controller having four Single Input Single Output (SISO) proportional-integral (PI) controllers.

In particular, the two load-dependent controllers are connected in parallel with one another. What may be achieved with the aid of the four SISO PI controllers (two controllers for each channel of the two-channel magnetic resonance imaging system) is that the settling time is accelerated and the lag of an MRI recording is thus improved.

In the context of an additional development, the signals are decoupled upstream of the amplification system.

In particular, a decoupling component may be connected upstream of the amplification system. By way of example, with the aid of the decoupling component it is provided that a static portion in the signal is reduced or suppressed and/or that the values are scaled to a predefined extent.

In a next development, the load situation is determined on the basis of at least one of the following parameters: (1) the size of the patient; (2) the weight of the patient; (3) a region or organ to be examined; (4) a position of the examination table; (5) a position of the body coil for carrying out the MRI measurement; and (6) a position of the patient in relation to the examination table.

In one configuration, the setting of the amplification system is carried out during an open-loop measurement.

An open-loop measurement (also designated as open-loop operation) may concern a measurement that serves for setting the amplification system or the control circuit. This may be effected depending on the load situation in such a way that e.g. a patient occupies a predefined position in the MRI system and measurements are carried out before the actual MRI examinations in order to set the MRI system in an optimized manner for the imminent measurement.

In an alternative embodiment, an MRI measurement with the patient is carried out after the open-loop measurement.

In a next configuration, the control circuit is adapted during the MRI measurement.

Even during the MRI measurements, the control circuit may be adapted and the quality of the measurements obtained may thus be improved.

In one configuration, moreover, the load situation is determined by the open-loop measurement.

The load situation may also be (concomitantly) determined depending on parameters that are determined during the open-loop measuring. In other words, parameters that are determined during the open-loop measurement may also be used in order to determine the load situation and thus, depending on the load situation, to adapt the control circuit or the amplification system via the control circuit.

The abovementioned object is also achieved by an apparatus for driving a two-channel magnetic resonance imaging system including an amplification system, wherein the amplification system is adaptable by a control circuit depending on a load situation.

For this purpose, the control circuit may be embodied as a processor unit and/or an at least partly hardwired or logical circuit arrangement designed, for example, in such a way that the method as described herein may be carried out. In this case, it is possible to use any type of processor or computer with correspondingly required peripherals (memory, input/output interfaces, input-output devices, etc.).

The above explanations concerning the method correspondingly apply to the apparatus. The apparatus may be embodied in one component or in a distributed manner in a plurality of components.

In one development, the control circuit has a feedback of the output signal of the amplification system, in particular, to the input of the amplification system.

In one development, moreover, at least one controller is provided in a feedforward branch of the control circuit, with the aid of which at least one controller an amplification of the amplification system is settable and with the aid of which at least one controller a settling time of the amplification system is settable.

The abovementioned object is also achieved by a two-channel magnetic resonance imaging system including one of the apparatuses described here.

The solution presented here furthermore includes a computer program product that is directly loadable into a memory of a digital computer, including program code parts suitable for carrying out acts of the method described here.

Furthermore, the abovementioned problem is solved by a computer-readable storage medium, e.g. of an arbitrary memory, including instructions (e.g. in the form of program code) that are executable by a computer are suitable to the effect that the computer carries out acts of the method described here.

DETAILED DESCRIPTION

An MIMO (Multiple Input Multiple Output) system denotes a system having a plurality of inputs and a plurality of outputs or having a plurality of input variables and a plurality of output variables. The term multi-variable system may be used as well. Systems having exactly one input variable and one output variable are designated as SISO (Single Input Single Output) system.

A RFPA system includes a power amplifier in a radio-frequency range, e.g., in a high-frequency range. One radio-frequency signal (also designated as RF signal) is amplified per channel, wherein the RF signal has a specific amplitude and phase.

A two-channel RFPA system is provided below. From the standpoint of open-loop or closed-loop control, a two-channel RFPA system corresponds to a 4×4 MIMO system, including two channels each for amplitude and phase of the settable RF signal.

Figure 1:
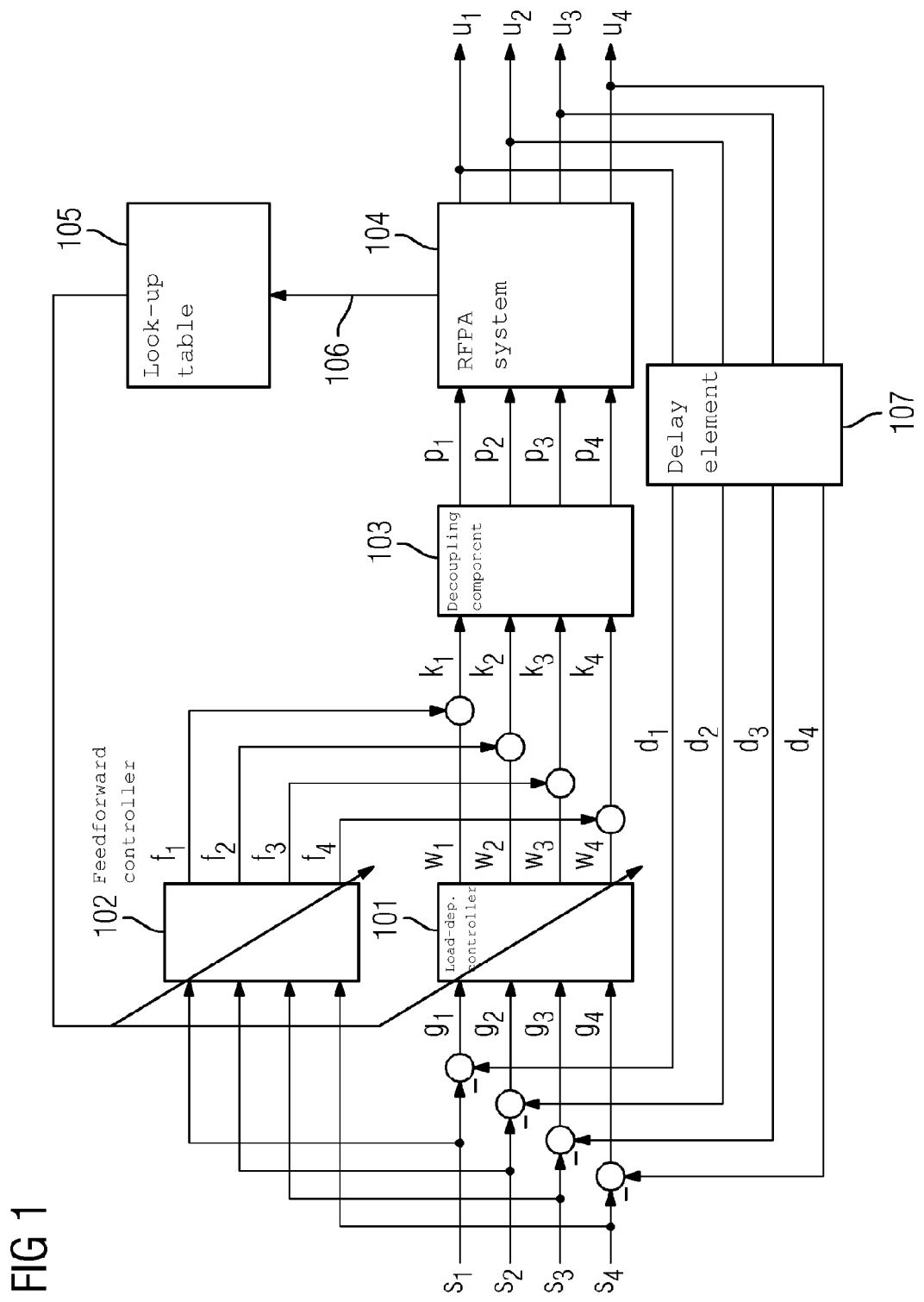
FIG. 1 depicts an embodiment of a schematic block diagram for a RFPA system with closed-loop control for use in a two-channel MRI system.

FIG. 1 depicts a schematic block diagram of an RFPA system with closed-loop control for use in a two-channel MRI system.

The desired or reference values $s_i$ where $i=1 \ldots 4$ are applied to a load-dependent feedforward controller 102. Furthermore delayed output values $d_i$ ($i=1 \ldots 4$) are subtracted from the desired values and the result is fed in the form of values:

$$g_i = s_i - d_i \text{ where } i=1 \ldots 4$$

to a load-dependent controller 101 having four SISO PI controllers, one for each channel i.

A PI controller, also designated as a proportional-integral controller, includes the portions of a proportional element and an integral-action element.

Output values $f_i$ of the controller 102 are combined with output values $w_i$ of the controller 101 to form values $k_i$, e.g.:

$$k_i = w_i + f_i \text{ where } i=1 \ldots 4,$$

and fed to a decoupling component 103. By way of example, with the aid of the decoupling component 103 it is provided that a static portion in the signal $k_i$ is reduced or suppressed and/or that the values $k_i$ are scaled to a predefined extent.

The decoupling component 103 decouples with respect to an RFPA system 104. In other words, as a result of the use of the decoupling component upstream of the RFPA system, this corresponds functionally to four SISO systems decoupled from one another.

At the output of the decoupling system, values $p_i$ are correspondingly provided to the RFPA system 104.

The decoupling component 103 decouples the inputs and outputs of the RFPA system. For example, each signal of the four input signals corresponds to one of the four output signals of the RFPA system, and the couplings originally present between the input and output signals are thus reduced or (largely) eliminated. The 4×4 RFPA system is thus subdivided into four 1×1 subsystems. The scaling is effected, for example, in such a way that each subsystem of the four 1×1 subsystems has the same DC voltage amplification.

The decoupling component 103 is determined depending on the load situation. This is effected by introducing an act successively upon the temporary switching-off of the closed-loop control to the desired voltage signals $s_1$, $s_2$, $s_3$ and $s_4$ and determining the output voltages $u_1$, $u_2$, $u_3$ and $u_4$. The DC voltage amplification (a 4×4 matrix) of the RFPA system may be determined from the act responses. In the simplest case, the decoupling component 103 is the inverse of the DC voltage amplification matrix. Alternatively, the inverse of the DC voltage amplification matrix may also be multiplied by four input scaling factors.

With the aid of the load situation or the experimentally determined DC voltage amplification matrix of the RFPA system 104, corresponding information 106 is communicated to a look-up table 105, with the aid of which the information 106 is converted into an associated setting for the controllers 101 and 102. This may take place in the context of an open-loop measurement and/or while an examination is being carried out.

The RFPA system 104 provides output values $u_i$ (e.g. in the form of output voltages), which are also converted into the delayed output values $d_i$ by a delay element 107.

Consequently, the RFPA system 104 is driven efficiently, and by the (feedback) information 106, it is provided that the RFPA system is operated in an optimized manner for the respective load situation.

The controller 101 is used in this case to reduce or to eliminate control errors in the settled state.

The controller 102 is used to accelerate the settling time and thus to improve a lag during the MRI recording.

The decoupling component 103 includes, for example, a static decoupling and scaling matrix, which serves to reduce (or at least proportionally), avoid crosstalk between the four channels.

In order to enable efficient MRI measurements for different load situations and thus to improve the performance and efficiency of the MRI system, it is possible to provide different feedforward control amplification matrices in the controller 102 and, if appropriate, correspondingly matching settings for the controller 101 (parameterizations of the PI controllers), which are selected depending on the information 106, which is in turn determined depending on the respective load situations. In this regard, the information 106 may serve to address an entry in the look-up table 105 that include a corresponding setting of the controllers 101 and 102. This setting is thereupon adopted for the controllers 101, 102.

Depending on the load of the RFPA system 104, it is thus possible to choose a suitable amplification by the look-up table 105. It is thus possible to achieve the required fast settling time depending on the respective specific load situation and at the same time to provide a good quality of the recordings.

In particular, the RFPA system may be set such that, e.g., the following predefined stipulations are fulfilled: (1) For a step response, a settling time (for reaching a tolerance band amounting to e.g. 5% around a target value) is less than 10 microseconds (without steady-state error portion). (2) A predefined maximum voltage at the output of the amplifier is not exceeded. (3) The predefined stipulations (1) and (2) are complied with for different load situations. In this case, the load situations correspond, e.g., to different patients, to their organs to be examined, and the different positions during the MRI examination.

The load situation may depend on different factors. By way of example, the size of the patient may be estimated in relation to a region to be examined. Such an estimation may take account of at least one of the following parameters: (1) the weight of the patient, (2) the region to be examined, e.g., depending on a position of an examination table and/or on a position of the patient on the examination table (e.g., lying on the back/stomach, lying on the right/left side), and (3) an open-loop measurement.

During the open-loop measurement, an actual load-dependent system behavior may be measured and the parameters of the control loop may be adjusted in such a way that an optimized dynamic system response is achieved.

The actual examination (MRI measurement) of the patient is effected after said open-loop measurement.

Figure 2:
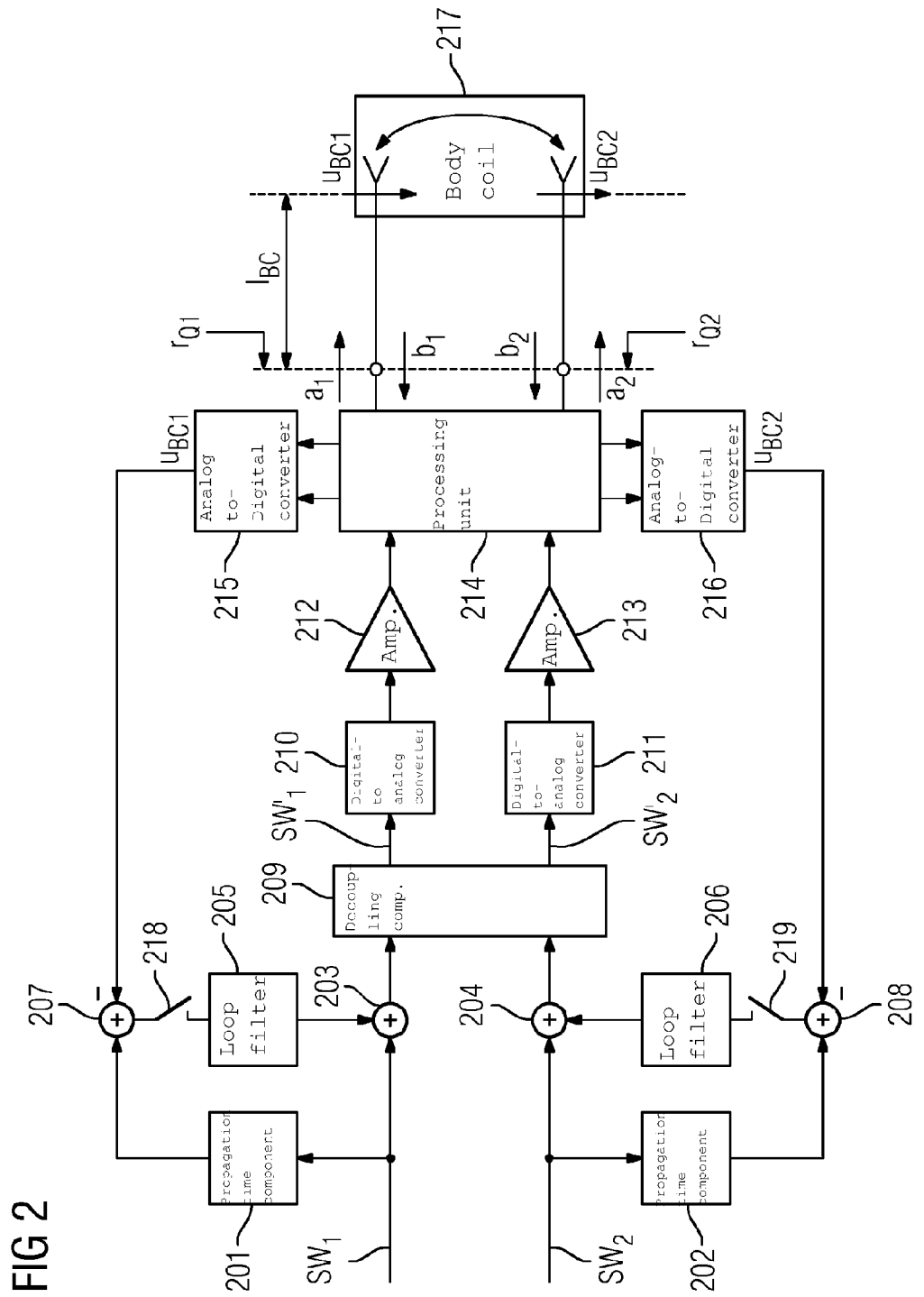
FIG. 2 depicts an alternative embodiment of a schematic block diagram of a two-channel MRI system.

FIG. 2 shows a schematic diagram of a two-channel MRI system.

A desired value $sw_1$ is applied to a propagation time component 201 and to an adder element 203, and the result of the propagation time component 201 is passed to an adder element 207. The result of the adder element 207 is passed via a switch 218 to a loop filter 205 to the adder element 203. The output of the adder element 203, that is to say the addition of the desired value $sw_1$ to the output value of the loop filter 205, is fed to a decoupling component 209.

A desired value $sw_2$ is applied to a propagation time component 202 and to an adder element 204, and the result of the propagation time component 202 is passed to an adder element 208. The result of the adder element 208 is passed via a switch 219 to a loop filter 205 to the adder element 204. The output of the adder element 204, that is to say the addition of the desired value $sw_2$ to the output value of the loop filter 206, is likewise fed to the decoupling component 209.

Consequently, by the decoupling component 209, a modified (desired) value $sw_1'$ arises from the desired value $sw_1$ and a modified (desired) value $sw_2'$ correspondingly arises from the desired value $sw_2$.

The value $sw_1'$ is fed via a digital-to-analog converter 210 and an amplifier 212 to a processing unit 214. The value $sw_2'$ is correspondingly fed via a digital-to-analog converter 211 and an amplifier 213 to the processing unit 214.

The processing unit 214 communicates incoming waves $a_1$ and $a_2$ via a cable of length $l_{BC}$ to a body coil 217.

The body coil 217 supplies incoming waves $b_1$ and $b_2$ or voltage values $U_{BC1}$ and $U_{BC2}$ to the processing unit 214.

The voltage $U_{BC1}$ is fed by the processing unit 214 via an analog-to-digital converter 215 as a digital measured actual value to the adder element 207 and is subtracted from the output value of the propagation time component 201. The voltage $U_{BC2}$ is correspondingly fed by the processing unit 214 via an analog-to-digital converter 216 as a digital measured actual value to the adder element 208 and is subtracted from the output value of the propagation time component 202.

The desired values in FIG. 2 are complex signals including a real part and an imaginary part.

The modified desired values $sw_1'$ and $sw_2'$ arise from the values shown in FIG. 1 as follows:

$$sw_1' = p_1 + i*p_2,$$

$$sw_2' = p_3 + i*p_4.$$

The output voltages $U_{BC1}$ and $U_{BC2}$ (voltages across the body coil 217) determined arise from the values illustrated in FIG. 1 as follows:

$$u_{BC1} = u_1 + i*u_2,$$

$$u_{BC2} = u_3 + i*u_4.$$

The relationship between input and output variables may be described by a complex 2×2 matrix K (coupling matrix):

$$\begin{pmatrix} u_{BC1} \\ u_{BC2} \end{pmatrix} = \underline{K} \cdot \begin{pmatrix} sw'_1 \\ sw'_2 \end{pmatrix}$$

The matrix K depends on the load situation of the body coil 217 and on output reflection coefficients $r_{Q1}$ and $r_{Q2}$ of the power amplifier. The matrix K may be determined in the context of the open-loop measurement (adaptation) before the actual examination (recording).

The open-loop measurement may be effected by determining a scattering matrix of the body coil used and determining the matrix K with the aid of estimated output reflection coefficients of the power amplifier. This approach is suitable in particular because the scattering matrix is also required and therefore predetermined for the specific absorption rate (SAR) monitoring. Therefore, only a small additional outlay with regard to calculation and communication is required.

The open-loop measurement may also be effected by directly determining the matrix K. In this case, the actual properties of the power amplifier may be taken into account. An inverse of the matrix K for the static decoupling and scaling may be used (also cf. the decoupling component 103 in FIG. 1) to enable optimized dynamic measurements of the MRI system.

The explanations below also apply in particular to closed-loop control based on voltages $u_{BC}$ across the body coil. This corresponds to an exemplary controlled variable. Alternatively or additionally, e.g. the incoming waves may also be used as a controlled variable.

Provided that no further coupling takes place in the processing unit 214 itself and the latter itself is (virtually) free of inherent reflection, the incoming waves arise as:

$$\begin{pmatrix} a_1 \\ a_2 \end{pmatrix} = \underline{S} \cdot \begin{pmatrix} sw'_1 \\ sw'_2 \end{pmatrix} = \frac{1}{\text{term}} \cdot \begin{pmatrix} \tau_1(1-s_{22}r_{Q2}) & \tau_2 s_{12} r_{Q1} \\ \tau_1 s_{21} r_{Q2} & \tau_2(1-s_{11}r_{Q1}) \end{pmatrix} \cdot \begin{pmatrix} sw'_1 \\ sw'_2 \end{pmatrix}$$

where:

term = $1 - r_{Q1}s_{11} - r_{Q2}s_{22} + r_{Q1}r_{Q2} \cdot \det(S_{BC})$, wherein $\tau_i$ (i=1,2) denotes the respective path transmission between the desired variables $sw_i'$ and a calibration plane of the scattering matrix of the body coil 217 relative to the calibration plane and the (nonlinear) reflection factors $r_{Qi}$ of the power amplifiers (likewise transformed into the calibration plane)

$$\underline{S}_{BC} = \begin{pmatrix} s_{11} & s_{12} \\ s_{21} & s_{22} \end{pmatrix}.$$

Consequently, the outgoing waves arise from the incoming waves via the scattering matrix of the body coil 217:

$$\begin{pmatrix} b_1 \\ b_2 \end{pmatrix} = \underline{S}_{BC} \cdot \begin{pmatrix} a_1 \\ a_2 \end{pmatrix}$$

with a transmission phase:

$$\varphi_{BC} = 2\pi \frac{l_{BC}}{\lambda}$$

which results in:

$$\begin{pmatrix} u_{BC1} \\ u_{BC2} \end{pmatrix} = e^{-j\varphi_{BC}} \cdot \begin{pmatrix} a_1 \\ a_2 \end{pmatrix} + e^{+j\varphi_{BC}} \cdot \begin{pmatrix} b_1 \\ b_2 \end{pmatrix}$$

and thus in:

$$\begin{pmatrix} u_{BC1} \\ u_{BC2} \end{pmatrix} = \underbrace{(e^{-j\varphi_{BC}} \cdot \underline{E} + e^{+j\varphi_{BC}} \cdot \underline{S}_{BC}) \cdot \underline{S}}_{\underline{K}} \cdot \begin{pmatrix} sw'_1 \\ sw'_2 \end{pmatrix}.$$

A decoupling matrix D may provide that during the open-loop measurement (e.g., during open-loop operation) the following relationship holds true:

$$\begin{pmatrix} u_{BC1} \\ u_{BC2} \end{pmatrix} = \underline{K} \cdot \underline{D} \cdot \begin{pmatrix} sw_1 \\ sw_1 \end{pmatrix} \stackrel{!}{=} \begin{pmatrix} sw_1 \\ sw_1 \end{pmatrix}.$$

which yields as a condition:

$D = K^{-1}$.

If the control loops of the systems decoupled are closed, then both operate independently of one another. This holds true, in particular, until the amplitudes become high enough that the nonlinear output reflection factors differ from the small-signal value on which the decoupling is based.

Under specific boundary conditions, it may happen that the matrix K becomes non-invertible, or the inversion becomes at least numerically unstable. This is manifested in a determinant of the matrix K whose value is zero or at least very close to the value zero.

From a physical viewpoint, the voltage $u_{BC2}$ in this case differs from the voltage $u_{BC1}$ only in a single complex factor independently of the combination of the two exciting signals. Such a case may be prevented in practice, since otherwise the system would become unstable upon the least change in the scattering matrix during operation or upon a change in the output reflection factor as a result of strong modulation.

With the aid of the closed representation of the decoupling matrix:

$$\underline{D} = \frac{1}{e^{-2j\varphi_{BC}} + s_{11} + s_{22} + e^{-2j\varphi_{BC}}\det(\underline{S}_{BC})} \cdot \begin{pmatrix} z_{11} & z_{12} \\ z_{21} & z_{22} \end{pmatrix}$$

where $$z_{11} = \frac{e^{-j\varphi_{BC}} + e^{j\varphi_{BC}}s_{22} - r_{Q1}[e^{-j\varphi_{BC}}s_{11} + e^{j\varphi_{BC}}\det(\underline{S}_{BC})]}{\tau_1};$$

$$z_{12} = \frac{-s_{12}(r_{Q1}e^{-j\varphi_{BC}} + e^{j\varphi_{BC}})}{\tau_1};$$

$$z_{21} = \frac{-s_{21}(r_{Q2}e^{-j\varphi_{BC}} + e^{j\varphi_{BC}})}{\tau_2}$$

and $$z_{21} = \frac{e^{-j\varphi_{BC}} + e^{j\varphi_{BC}}s_{11} - r_{Q2}[e^{-j\varphi_{BC}}s_{22} + e^{j\varphi_{BC}}\det(\underline{S}_{BC})]}{\tau_2}$$

it can be discerned that the common denominator term must not become zero and that this condition is independent of the output reflection factors and is dependent only on the scattering matrix of the body coil and the electrical length $l_{BC}$ with respect to the voltage plane of the body coil.

Accordingly, the following parameters may be known for determining the decoupling matrix D: (1) the scattering matrix of the body coil relative to the calibration plane (this may be measured for each load situation); (2) the small-signal output reflection factor of the power amplifiers transformed into the calibration plane (this may be measured once, for example); (3) the length $l_{BC}$ between the calibration plane and the reference plane of the voltages of the body coil (this involves a structural predefined specification, for example, which may be correspondingly adopted).

The efficiency of the open-loop measurement may additionally be increased by the parameters being adapted or estimated taking account of (1) the frequency, (2) the waveform, and/or (3) the magnitude of at least one subsequent pulse (or signal).

As already explained, the actual examination (MRI measurement) of the patient may be effected after the open-loop measurement. In this case, the MRI measurement may also be subject to temporal fluctuations that may not have been taken into account or compensated for during the preceding calibration (open-loop measurement). However, it is possible for changes in the system parameters also to be detected during the MRI measurement, by virtue of said system parameters being compared with the input and output variables of the RFPA system in the open-loop measurement. On the basis of such additional information during the MRI measurement itself, it is possible to adaptively track (set) the parameters. By way of example, a phase shift that occurs on an amplifier channel via the connected antenna may be compensated for by the feedback loop and the feedforward controller. By such (e.g. continuous) adaptation, the dynamic behavior of the control loop, even during the MRI measurement, may be constantly improved.

Consequently, the approach presented here enables the flexible and dynamic setting and tracking (e.g. of an amplification) of the RFPA system, to be precise depending on the actual load situation. In this case, the load situation may be dependent, in particular, on the weight of a patient, the position of the examination table, the position of the patient on the examination table, the organ to be examined, the previous measurement data and other parameters obtained in the course of the MRI measurement(s).

A list of reference signs used within the above-described embodiments are provided in the table below.

| | |
|---|---|
| 101 | Load-dependent controller (including four SISO PI controllers) |
| 102 | Load-dependent feedforward controller |
| 103 | Decoupling component |
| 104 | RFPA system |
| 105 | Look-up table |
| 106 | (Load-situation-dependent) information |
| 107 | Delay element |
| 201 | Propagation time component |
| 202 | Propagation time component |
| 203 | Adder element |
| 204 | Adder element |
| 205 | Loop filter |
| 206 | Loop filter |
| 207 | Adder element |
| 208 | Adder element |
| 209 | Decoupling component |
| 210 | Digital-to-analog converter |
| 211 | Digital-to-analog converter |
| 212 | Amplifier |
| 213 | Amplifier |
| 214 | Processing unit |
| 215 | Analog-to-digital converter |
| 216 | Analog-to-digital converter |
| 217 | Body coil |
| 218 | Switch |
| 219 | Switch |

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for setting an amplification system for a two-channel magnetic resonance imaging system, the method comprising:
   determining a load situation, by the amplification system, with aid of an open-loop measurement; and
   adapting the amplification system by a control circuit, wherein the amplification system is adapted by the control circuit depending on the load situation.

2. The method as claimed in claim 1, wherein the control circuit has a feedback of an output signal of the amplification system to an input of the amplification system.

3. The method as claimed in claim 2, further comprising:
   setting, with the amplification system, at least one controller of the two-channel magnetic resonance imaging system depending on the load situation.

4. The method as claimed in claim 2, further comprising:
   carrying out a delay of the output signal out during the feedback.

5. The method as claimed in claim 4, further comprising:
   setting, with the amplification system, at least one controller of the two-channel magnetic resonance imaging system depending on the load situation.

6. The method as claimed in claim 1, further comprising:
   setting, with the amplification system, at least one controller of the two-channel magnetic resonance imaging system depending on the load situation.

7. The method as claimed in claim 6, wherein the at least one controller comprises a load-dependent feedforward controller for setting an amplification of the amplification system.

8. The method as claimed in claim 7, wherein the at least one controller comprises a further load-dependent controller having four Single Input Single Output (SISO) proportional-integral (PI) controllers.

9. The method as claimed in claim 6, wherein the at least one controller comprises a further load-dependent controller having four Single Input Single Output (SISO) proportional-integral (PI) controllers.

10. The method as claimed in claim 1, further comprising:
    decoupling signals upstream of the amplification system.

11. The method as claimed in claim 1, wherein the load situation is determined on the basis of at least one of the following parameters:
- a size of a patient;
- a weight of the patient;
- a region or an organ to be examined;
- a position of an examination table;
- a position of a body coil for carrying out a magnetic resonance imaging (MRI) measurement; or
- a position of the patient in relation to the examination table.

12. The method as claimed in claim 1, further comprising: carrying out the setting of the amplification system during the open-loop measurement.

13. The method as claimed in claim 12, further comprising:
carrying out a magnetic resonance imaging (MRI) measurement with the patient after the open-loop measurement.

14. The method as claimed in claim 13, wherein the control circuit is adapted during the MRI measurement.

15. An apparatus for driving a two-channel magnetic resonance imaging system, the apparatus comprising:
- a control circuit;
- an amplification system configured to determine a load situation with aid of an open-loop measurement,
- wherein the amplification system is adaptable by the control circuit depending on the load situation.

16. The apparatus as claimed in claim 15, wherein the control circuit has a feedback of an output signal of the amplification system to an input of the amplification system.

17. The apparatus as claimed in claim 15, wherein at least one controller is provided in a feedforward branch of the control circuit, wherein with aid of the at least one controller, an amplification of the amplification system is settable and a settling time of the amplification system is settable.

18. A two-channel magnetic resonance imaging system comprising:
- an amplification system having a control circuit and at least one controller,
- wherein the amplification system is configured to determine a load situation with aid of an open-loop measurement,
- wherein the amplification system is adaptable by the control circuit depending on the load situation,
- wherein the control circuit has a feedback of an output signal of the amplification system to an input of the amplification system, and
- wherein the at least one controller is provided in a feedforward branch of the control circuit, wherein with the at least one controller, an amplification of the amplification system is settable and a settling time of the amplification system is settable.

* * * * *